United States Patent [19]

Box

[11] 4,421,760
[45] Dec. 20, 1983

[54] β-LACTAM ANTIBIOTIC, ITS PREPARATION AND USE

[75] Inventor: Stephen J. Box, Horsham, England

[73] Assignee: Beecham Group Limited, England

[21] Appl. No.: 274,464

[22] Filed: Jun. 17, 1981

[30] Foreign Application Priority Data

Jul. 2, 1980 [GB] United Kingdom ............... 8021730

[51] Int. Cl.³ ................... C07D 487/04; A61K 31/40
[52] U.S. Cl. .............................. 424/274; 260/245.2 T;
424/114; 435/119
[58] Field of Search .................. 260/245.2 T; 424/274

[56] References Cited

U.S. PATENT DOCUMENTS 4,113,856  9/1978  Cole et al. ................... 260/245.2 T
4,146,610  3/1979  Cole et al. ................... 260/245.2 T Primary Examiner—Mary C. Lee
Attorney, Agent, or Firm—Jacobs & Jacobs

[57] ABSTRACT

The compound of the formula (VI):

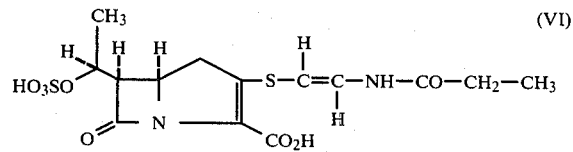

pharmaceutically acceptable salts and pharmaceutically acceptable esters thereof, are useful for their antibacterial activity and for their β-lactamase inhibitory activity. They may be combined in a synergistically effective amount with a penicillin or cephalosporin for the treatment of bacterial infections in humans and animals.

74 Claims, No Drawings

β-LACTAM ANTIBIOTIC, ITS PREPARATION AND USE

The present invention relates to a new antibiotic, its preparation and to compositions containing it.

British Pat. Nos. 1,467,413, 1,489,235 and 1,483,142 disclose that fermentation of *Streptomyces olivaceus* can lead to the preparation of antibiotics named MM 4550A, MM 13902 and MM 17880 which have the formulae (I), (II) and (III) respectively:

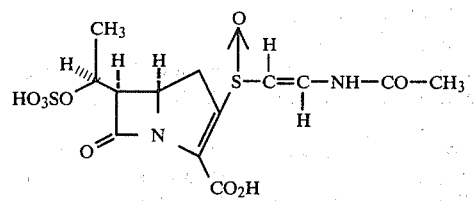

(I)

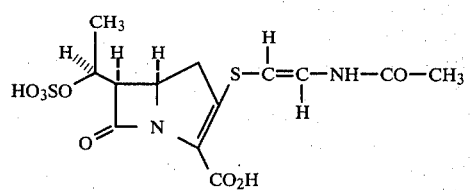

(II)

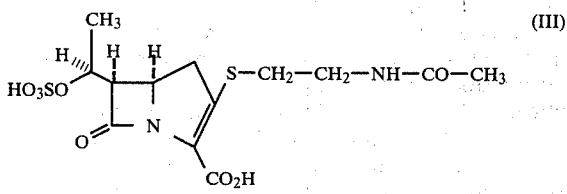

(III)

Belgian Pat. No. 864570 discloses that further antibiotics may be obtained from the fermentation broth of *Streptomyces olivaceus;* these have the formulae (IV) and (V):

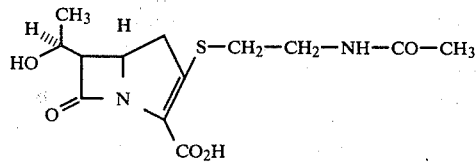

(IV)

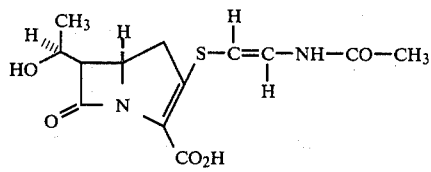

(V)

None of these patents contained any suggestion that a further antibiotic could be obtained from the fermentation broth of *Streptomyces olivaceus*. We have now found that in addition to the foregoing compounds strains of *Streptomyces olivaceus* produce a further antibacterially active compound which has the formula (VI):

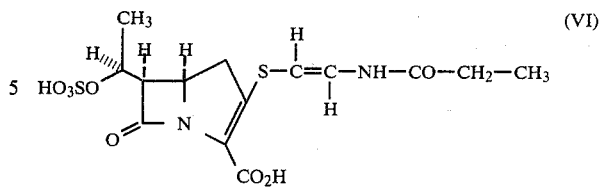

(VI)

Accordingly the present invention provides the compound of the formula (VI) and its salts and esters. Preferably for use in pharmaceutical compositions such salts and esters are pharmaceutically acceptable.

Suitable salts of the compound of the formula (VI) include the pharmaceutically acceptable alkali and alkaline earth metal salts such as the sodium, potassium, calcium, magnesium, ammonium and substituted ammonium salts such as the trimethylammonium, dimethylammonium, tetramethylammonium and pyrrolidine salts. Particularly suitable salts are the sodium and potassium salts. Di-salts such as the di-sodium or di-potassium salts are especially advantageous due to their relative ease of preparation. Salts of the compound of the formula (VI) are a favoured aspect of this invention as they tend to be more stable than the parent acid per se.

Salts of the compound of the formula (VI) formed with ions which are not pharmaceutically acceptable are useful as they may serve as intermediates in the preparation of pharmaceutically acceptable salts by ion-exchange, or they may be useful as intermediates in the preparation of esters. An example of such a salt is the lithium salt.

The salts of this invention may be in crystalline or non-crystalline form and when crystalline may be solvated for example hydrated.

The compound of the formula (VI) may be provided as an ester formed at the carboxylic acid group. Thus suitable esters include those of the formula (VII):

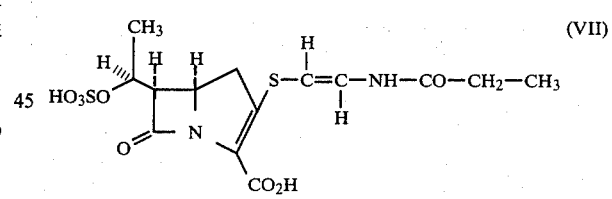

(VII)

or a sulphate salt thereof, wherein R is an esterifying group. Suitable esters of the compound of the formula (VII) include those convertible to the free acid or salt thereof by biological methods such as enzymatic hydrolysis and in-vivo hydrolysis, and those convertible by chemical methods such as hydrogenolysis, hydrolysis, electrolysis or photolysis.

Suitably R is an alkyl, alkenyl, alkynyl aryl or aralkyl group which may be substituted if desired. Preferably the alkyl, alkenyl and alkynyl groups and the alkyl portion of the aralkyl group contain up to 6 carbon atoms. Suitable substituents which may be included in the group R include halogen atoms and $C_{1-6}$ alkoxy, $C_{1-6}$ alkanoyl, hydroxy, $C_{1-6}$ acyloxy for example $C_{1-6}$ alkanoyloxy, $C_{1-6}$ alkylamino and di($C_{1-6}$) alkylamino groups.

More suitably the carboxylic acid is esterified by a group of the sub-formula (a), (b), (c), (d), (e) or (f):

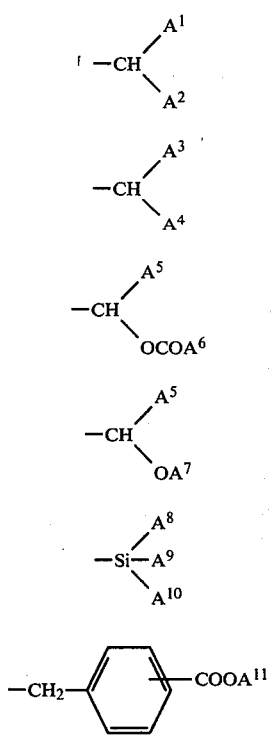

wherein $A^1$ is a hydrogen atom, $C_{1-6}$ alkanoyl or an $C_{1-5}$ alkyl group optionally substituted by $C_{1-7}$ alkoxy or $C_{1-7}$ carboxylic acyloxy, or an alkenyl or alkynyl group of up to 5 carbon atoms; $A^2$ is a hydrogen atom or a methyl group; $A^3$ is a phenyl group or a phenyl group substituted by a fluorine, chlorine or bromine atom or a nitro, $C_{1-3}$ alkyl or $C_{1-3}$ alkoxy group; $A^4$ is a hydrogen atom or a phenyl group or phenyl group substituted by a fluorine, chlorine or bromine atom or a nitro, $C_{1-3}$ alkyl or $C_{1-3}$ alkoxy group; $A^5$ is a hydrogen atom or a methyl group; $A^6$ is a $C_{1-6}$ alkyl, phenyl, phenoxy, phenyl $(C_{1-3})$ alkyl, phenyl $(C_{1-3})$ alkoxy or $C_{1-6}$ alkoxy group or $A^5$ is joined to $A^6$ to form a phthalidyl, dimethylphthalidyl or dimethoxyphthalidyl group; $A^7$ is a $C_{1-4}$ alkyl, phenyl, chlorophenyl or nitrophenyl group; $A^8$ is a $C_{1-4}$ alkyl or phenyl group; $A^9$ is a $C_{1-4}$ alkyl or phenyl group; $A^{10}$ is $C_{1-4}$ alkyl; and $A^{11}$ is $C_{1-4}$ alkyl: or $CHA^1A^2$ is a phenacyl or bromophenacyl group.

Favourably $A^1$ is a hydrogen atom or a methyl, ethyl, vinyl or ethenyl group. Favourably $A^2$ is a hydrogen atom. Favourably $A^3$ is a phenyl, p-bromophenyl, p-methoxyphenyl or p-nitrophenyl group. Favourably $A^4$ is a hydrogen atom. Favourably $A^6$ is a methyl, t-butyl or ethoxy group or is joined to $A^5$. Favourably $A^7$ is a methyl group. Favourably $A^5$ is a hydrogen atom.

Preferred groups of the sub-formula (a) include the methyl, ethyl and acetonyl groups.

Preferred groups of the sub-formula (b) include the benzyl and p-nitrobenzyl groups.

When $A^5$ is hydrogen, suitably $A^6$ is selected from methyl, ethyl, n-propyl, iso-propyl, n-butyl, tert-butyl, phenyl, benzyl, methoxy, ethoxy, n-propyloxy and iso-propyloxy. Preferably $A^6$ is tert-butyl. Preferred groups of the sub-formula (c) include the acetoxymethyl, pivaloyloxymethyl, ethoxycarbonyloxymethyl, phthalidyl, α-ethoxycarbonyloxyethyl and α-acetoxyethyl groups. These esterifying groups are favoured as they tend to form in-vivo hydrolysable esters.

A preferred group of the sub-formula (d) is the methoxymethyl group.

Preferred groups of the sub-formula (e) include the trimethylsilyl, tert-butyldimethylsilyl and tert-butyldiphenylsilyl groups.

A preferred group of the sub-formula (f) is p-methoxycarbonylbenzyl.

Particularly preferred esterifying groups are the p-nitrobenzyl and phthalidyl groups.

The in-vivo hydrolysable nature of the ester may be confirmed by administration to an animal such as a mouse or rat and determination of the presence of a compound of the formula (VI) or a salt thereof in the bllod or urine of the animal. Alternatively hydrolysis in human blood or serum may be determined.

Esters of the compound of the formula (VI) are useful intermediates in certain processes for the preparation of the free acid and its salts, and they also possess antibacterial activity.

Compounds of the formula (VI) wherein the sulphate moiety is esterified are envisaged primarily as intermediates. Suitable esters include the $C_{1-6}$ alkyl esters, for example the methyl or ethyl ester.

Since the compounds of the formula (VI) and its salts and esters are intended for use in pharmaceutical compositions it will be readily understood that they are provided in substantially pure form, for example at least 50% pure, more suitably 75% pure and preferably at least 90% pure (% on weight/weight basis). Impure preparations of the compounds of the formula (VI) and its salts and esters may be used for preparing the more pure forms used in the pharmaceutical compositions.

The present invention also provides a pharmaceutical composition which comprises a compound of the formula (VI) or a pharmaceutically acceptable salt or ester thereof and a pharmaceutically acceptable carrier.

Most suitably the compositions of this invention contain a pharmaceutically acceptable salt of a compound of the formula (VI) for example the sodium or potassium salt, preferably the di-sodium or di-potassium salt.

Alternatively the compositions of this invention contain an ester of a compound of the formula (VI). In-vivo hydrolysable esters tend to be more suitable than the less readily hydrolysable esters so that compositions of this invention more suitably comprise an in-vivo hydrolysable ester of a compound of the formula (VI), for example those stated hereinabove as being suitable in-vivo hydrolysable esters.

Such compositions may be in a form suitable for oral, topical or parenteral use. For example, tablets, capsules, creams, syrups, reconstitutable powders and sterile forms suitable for injection or infusion may be used. Such compositions may contain conventional pharmaceutically acceptable materials such as diluents, binders, colours, flavours, preservatives, and disintegrants in accordance with conventional pharmaceutical practice in a manner well known to those skilled in the formulation of antibiotics such as penicillins and cephalosporins.

The compound of formula (VI) or pharmaceutically acceptable salt or ester thereof may be present in the composition of the invention as sole therapeutic agent or it may be present together with a β-lactam antibiotic. Suitable β-lactam antibiotics include those known to be susceptible to β-lactamases and also having some intrinsic resistance to β-lactamases. Such β-lactam antibiotics include ampicillin, amoxycillin, benzylpenicillin, phenoxymethylpenicillin, propicillin, cephaloridine, cefoxitin, cephalothin, cephalexin, carbenicillin, ticarcillin and in-vivo hydrolysable esters of such compounds such as the phenyl, tolyl or indanyl esters of carbenicillin or ticarcillin or the acetoxymethyl, pivaloyloxymethyl or phthalidyl esters of ampicillin, benzylpenicillin, amoxycillin, cephaloridine, and cephaloglycin.

The ratio of the compound of the formula (VI) or pharmaceutically acceptable salt or ester thereof to $\beta$-lactam antibiotic is normally between 10:1 and 1:10, for example, between 4:1 and 1:4, more usually 2:1 to 1:3.

The total quantity of antibacterial agents present in any unit dosage form will normally be between 50 and 1500 mgs and will usually be between 100 and 1000 mgs.

Preferred unit dosage compositions according to this invention may be administered one or more times a day, for example, 2 to 4 times a day, in the treatment of diseases of the urinary tract, respiratory tract and soft tissues. Thus the compositions may be used in the treatment of such diseases as bronchitis, gonorrhea, otitus media, and mastitis.

The present invention also provides a process for the preparation of a compound of the formula (VI) or salt thereof which process comprises cultivating a producing strain of *Streptomyces olivaceus* or *Streptomyces gedanesis* and thereafter recovering the compound of the formula (VI) or salt thereof from the cultivation medium.

When used herein the term "*Streptomyces olivaceus*" is defined according to the classification of Hutter. R (in Systematic der Streptomyceten, S. Karger, Basle). Note that on this definition *Streptomyces fulvovoridis, Streptomyces flavus* and *Streptomyces flavovirens* may be regarded as being synonymous with *Streptomyces olivaceus*.

One strain of the organism *Streptomyces olivaceus* (256-13), for use in this process has been deposited on May 29, 1980 under accession number CBS 349.80 at Centraal Bureau voor Schimmelcultures (CBS), Baarn, Netherlands; the strain has also been deposited at the American type Culture Collection under number ATCC 31921; this strain or a high yielding mutant thereof is preferred. This strain is a mutant derived from *Streptomyces olivaceus* ATCC 31126 and is believed to have essentially the same morphological and taxonomical characteristics as described for ATCC 31126, for example in British Patent Specification Nos. 1,467,413 and 1,489,235. Other suitable strains are *Streptomyces Olivaceus* ATCC 21379, 21380, 21381, 21382 and 31126.

When used herein the term "mutant" includes any mutant strain which arises spontaneously or through the effect of an external agent whether that agent is applied deliberately or otherwise. Suitable methods of producing mutant strains are outlined in Techniques for the Development of Micro-organisms in "Radiation and Radio-isotopes for Industrial Micro-organisms", Proceedings of a Symposium, Vienna, 1973, page 241, International Atomic Energy Authority.

When used herein the term "cultivation" means the deliberate aerobic growth of an organism in the presence of assimilable sources of carbon, nitrogen, sulphur and mineral salts. Such aerobic growth may take place in a solid or semi-solid medium but in general it is preferable to use a liquid medium. General cultivation conditions for the growth of *Streptomyces olivaceus* are as described in British Patent Specification No. 1,467,413. General conditions for the growth of *Streptomyces gedanesis* are similar. Normally this cultivation process is adapted to the preparation of a salt, preferably a di-salt, rather than the parent acid.

In general, all isolation and purification procedures used in obtaining the desired antibiotic should take place at non-elevated temperatures, for example below 25° C. and more suitably below 20° C.

The desired antibiotic is normally obtained predominantly from the culture filtrate so that the preferred initial step in the isolation process is the removal of solid material from the fermentation, for example by filtration.

An impure preparation of the compound of the formula (VI) or salt thereof may be obtained from the culture filtrate by adsorbing the compound of the formula (VI) or salt thereof on to an active material such as active carbon and thereafter eluting the compound of the formula (VI) or salt thereof from the active material using a solvent such as aqueous acetone. Normally this procedure is performed on a di-basic salt of the compound of the formula (VI).

In an alternative procedure which is frequently more effective an impure preparation of a compound of the formula (VI) or a salt thereof may be obtained from the culture filtrate by extraction using a lipophilic ammonium salt and a water immiscible solvent. The compound of the formula (VI) may then be obtained as its substituted ammonium salt by evaporation of the water-immiscible solvent under reduced pressure. Preferably however the solution of the substituted ammonium salt is back extracted into an aqueous phase by using a solution of an alkali metal salt. The aqueous phase is then separated in conventional manner to afford usually a di-basic salt of the compound of the formula (VI).

The compound of formula VI in the form of its salt may also be obtained from the culture filtrate by contacting the clarified cultivation broth with a basic anion exchange resin.

The compound of the formula (VI) or its salts are then normally subjected to chromatography in order to produce material of acceptable purity.

In another aspect therefore this invention provides a process for the preparation of a compound of the formula (VI) or salt thereof which comprises chromatographically separating a solution of impure compound of the formula (VI) or salt thereof as hereinbefore described into fractions consisting essentially of a solution of the compound of the formula (VI) or salt thereof and other fractions and isolating the compound of the formula (VI) or salt thereof from solution.

By the terms "consisting essentially of a solution of a compound of the formula (VI) or salt thereof" it is meant that either the only antibiotic material present in that solution is a compound of the formula (VI) or salt thereof, or if any other antibiotic material is present then it is there to a lesser extent than the compound of the formula (VI) or salt thereof.

The chromatographic purification of the compound of the formula (VI) or salt thereof is best carried out using a salt, preferably a di-salt such as the di-sodium salt of the compound of the formula (VI). Salts of the compound of the formula (VI) are normally more soluble in aqueous and aqueous alcohol solvent systems than in highly lipophilic solvents and consequently it is preferred to use aqueous and aqueous alcohol solvent systems in the chromatographic purifications of this invention.

We have found that a satisfactory chromatographic procedure is to apply a solution of an impure preparation of the compound of the formula (VI) or salt thereof as hereinbefore described to an anion exchange column, and thereafter eluting therefrom with a solution of an electrolyte buffered to approximate neutrality, collecting the fractions containing the compound of the formula (VI) in salt form, applying the resulting solution to a resin which separates the inorganic materials and isolating the solid preparation of the salt of the compound (VI) from the resulting solution.

A suitable method of chromatographic purification uses an aqueous solution of a sodium salt buffered to approximate neutrality in conjunction with a basic ion-exchange resin. Thus an aqueous solution of sodium chloride buffered to about pH7 with a conventional buffer such as a phosphate buffer may be used in conjunction with support resins which contain secondary, tertiary or quaternary amino groups. Suitable support resins include basic ion-exchange celluloses and basic ion-exchange cross-linked dextrans, for example DEAE cellulose, DEAE Sephadex and QAE Sephadex.

A related suitable method of chromatographic purification uses a solvent system comprising a mixture of water and small quantities of a water immiscible organic solvent such as $C_{1-4}$ alkanol in conjunction with an inert support material such as silica gel or cellulose. Suitable solvent systems include aqueous isopropanol and aqueous n-butanol. For example an approximate 1:4 mixture of water and isopropanol may be used in conjunction with a cellulose support.

The product of the preceding procedures using ion-exchange resins frequently contains a high proportion of sodium chloride so that it is beneficial to de-salt the pooled solutions. De-salting may be effected by passing the solution through a bed of lipophilic material on to which the antibiotic is adsorbed but which does not adsorb the sodium chloride. Suitable lipophilic materials include polystyrene based polymeric adsorbants such as Amberlite XAD-4 and Diaion HP20. De-salting may also be effected by chromatography on suitable gel filtration agents such as cross-linked dextrans such as Sephadex G10, G15 and G25 and polyacrylamide gels such as Biogel P2. The antibiotic may be eluted from such materials using solvents such as water or aqueous methanol.

We have found it beneficial to subject the salts of the compound of the formula (VI) prepared by the previous methods, to further chromatographic separation techniques. One suitable form of chromatography for further purification is high performance liquid chromatography (h.p.l.c.), for example using an aqueous potassium phosphate buffered solution.

Of course it is to be understood that if desired further chromatography may be performed at any stage of the chromatographic purification procedure. We have found it most suitable to perform such further chromatography on Diaion HP20 or a chromatographically equivalent resin. Diaion HP20 is a styrene divinylbenzene copolymer in bead form having a macroreticular structure with a specific surface area of about 7.8 m²/g and a pore volume of 1.16 ml/g. Resins chromatographically equivalent to Diaion HP20 will normally be chemically and physically similar, that is they will generally be macroreticular resins based on styrene divinylbenzene copolymers and free of ionised groups.

When the desired solutions are obtained by the above processes the compound of the formula (VI) normally in the form of its di-salt may be obtained in solid form by the removal of the solvent under mild conditions, for example by evaporation or by freeze drying.

The presence of the compound (VI) in samples of culture filtrate or in chromatographic fractions in the above process, may be identified by h.p.l.c. using the following characteristic criteria:

(a) the eluant is detected by monitoring at approx 300 nm, which excludes detection of compounds which do not absorb at that position;

(b) a characteristic retention time as specified in description 1 hereinafter.

Identification of the compound can also be confirmed by a further chromatography after treatment of the sample with a reagent which degrades the compound such as a neutral solution of cysteine.

The following scheme shows a preferred sequence for obtaining the compound of the formula (VI) or salt thereof.

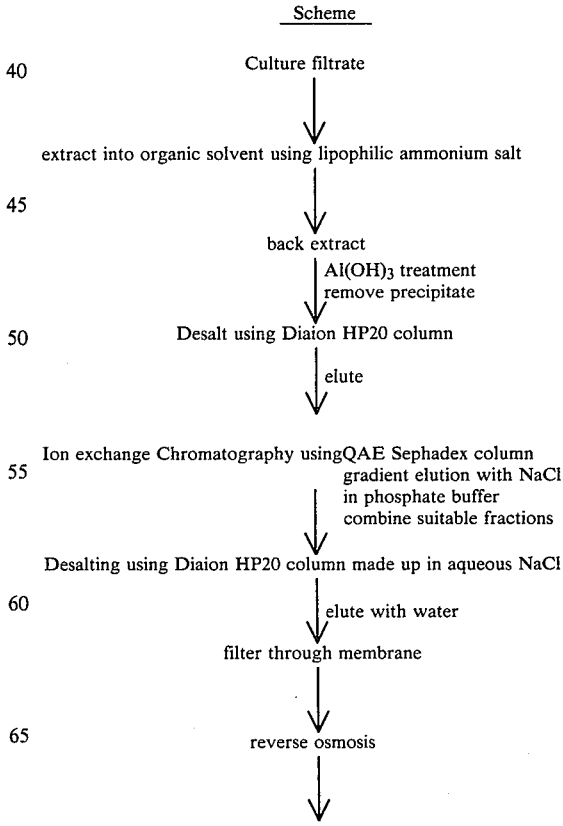

-continued
Scheme

Chromatography using Diaion HP20 column
| elute
| combine suitable fractions
| freeze dry
↓
Chromatography on Biogel P2
↓
Chromatography on Diaion HP20
↓
Chromatography on reverse phase hplc
↓
Desalt on Diaion HP20
↓
Di-sodium salt of the compound of the formula (VI).

The di-sodium salt obtained in this manner can be further purified if desired by using the chromatographic procedures described hereinbefore.

The present invention also provides a process for the preparation of the compound of the formula (VII) as hereinbefore defined or a sulphate salt or sulphate ester thereof which process comprises the esterification of the corresponding compound of the formula (VI).

Suitable methods of ester formation are those conventionally used to prepare esters of β-lactam containing compounds and include:

(a) the reaction of a di-salt of a compound of the formula (VI) with a compound of the formula (VIII):

R-Q  (VIII)

wherein R is as defined in relation to formula (VII) and Q is a displaceable group; and (b) the reaction of a mono-salt of a compound of the formula (VI) with a diazo compound.

Suitable di-salts of the compounds of the formula (VI) which may be reacted with compounds R-Q include alkali metal salts such as the sodium or potassium salts or other conventional salts such as the quaternary ammonium salts.

Suitably Q is a readily displaceable group and includes those atoms or groups known to be displaceable by carboxylate anions and includes chlorine, bromine and iodine atoms, sulphonic acid esters such as $OSO_2CH_3$ or $OSO_2C_6H_4CH_3$ and other conventional groups displaceable by nucleophilies.

A particularly suitable compound of the formula (VIII) is phthalidyl bromide. Other phthalidyl derivatives are also favoured.

This displacement reaction is normally carried out in an aprotic organic solvent such as dimethylformamide, dimethylsulphoxide, hexamethylphosphoric triamide, acetone, dioxane or acetonitrile optionally in the presence of a crown ether, and the like solvents and at a non-extreme temperature such as $-5°$ C. to $100°$ C. We have found that the reaction may suitably be carried out in anhydrous dimethylformamide at ambient temperature.

Those compounds in which the group R contains a chiral centre are generally initially formed as the R,S-form. Separation into the R- and S-isomers may be achieved by conventional methods such as chromatography, seeding out and crystallisation and the like.

The reaction of a mono-salt of a compound of the formula (VI) with a diazocompound is a mild method of making alkyl, aralkyl or substituted alkyl or aralkyl esters. The diazotization reaction may be performed under conventional reaction conditions, for example at a non-extreme temperature and in a conventional solvent. Such reactions are normally carried out at between $-5°$ C. and $100°$ C. and conveniently at ambient temperature. Suitable solvents for this reaction include $C_{1-4}$ alkanols such as methanol and ethanol and solvents such as tetrahydrofuran, dioxane and the like. These solvents will normally be present with a small amount of water which aids the solubility of the compounds of the formula (VI) in the solvent.

Aqueous ethanol has proved a particularly useful solvent for this reaction.

The mono ester mono quaternary ammonium salts of the compounds of the formula (VII) may also conveniently be prepared by the dissolution of a water soluble salt of a compound of the formula (VII) in water followed by the mixing of this solution with a solution of a quaternary ammonium halide in a water immiscible inert organic solvent. The organic solvent is then separated and evaporated to yield the quaternary ammonium salt. Suitably the organic solvent will be a halogen substituted hydrocarbon, such as methylene dichloride or chloroform, and the mixing of the two solutions will take place between $1°$ C. and $100°$ C., for example between $1°$ C. and $30°$ C. The two solutions will normally be mixed by shaking or stirring.

Salts of the compounds of the formula (VII) may be interconverted in conventional manner, for example by using ion exchange resins. Metal ion salts useful for this purpose include lithium, sodium and potassium salts.

The sulphate esters within the compounds of the formulae (VI)–(VII) may be prepared by esterification of a corresponding salt in conventional manner.

In another aspect the present invention provides a process for the preparation of a compound of the formula (VI) or salt or sulphate ester thereof which comprises the de-esterification of a compound of the formula (VII) or sulphate salt or sulphate ester thereof. Such de-esterification may be performed using conventional methods, for example biological methods such as enzymatic hydrolysis and in-vivo hydrolysis, and chemical methods such as hydrogenolysis, hydrolysis, electrolysis or photolysis.

The following Examples illustrate the invention. Note that in the Examples and Demonstration the compound of the formula (VI) or salt thereof is designated as MM 27696.

DESCRIPTION 1

Assay Methods

The presence of MM 27696 was detected using 2 methods.

1. Analytical High Performance Liquid Chromatography

Assay samples (25 μL) were loaded onto a 3.9×300 mm. Waters $C_{18}$ μBondapak reversed phase column, and the column eluted with 10% acetonitrile in 0.05 M ammonium phosphate buffer (pH 4.7) at 2 ml/minute. The eluant was monitored by a Cecil Model 212 u.v.

spectrophotometer using an 8-μL flow cell with 10 mm path length at 300 nm, MM 27696 had a retention time of 6.2 minutes in this system. Under these condition the compound MM 13902 (formula II above) has a retention time of 3.6 minutes.

2. Direct u.v. Measurement

MM 27696 has characteristic u.v. maxima at approximately 228 and 308 nm. Purified samples can be assayed using direct measurement of these adsorptions.

EXAMPLE 1

A spore suspension of *Streptomyces olivaceus* was used to inoculate 150 liters of sterilised seed stage medium contained in a 300 liter baffled stainless steel fermenter. The seed stage medium had the following composition:

|  | g/l |
|---|---|
| Glucose | 20.0 |
| Soybean Flour | 10.0 |
| Pluronic L81 antifoam prepared in tap water | 50 ml |

(The Soybean Flour was Arkasoy 50 supplied by the British Arkady Co. Ltd., Old Trafford, Manchester.) (The Pluronic L81 antifoam was supplied by Ugine Kuhlmann Chemicals Ltd. and used as a 10% suspension in soybean oil.)

The medium was steam sterilised in the fermenter.

After inoculation the seed stage culture was stirred at 110 r.p.m. with an 8.5 inch diameter vaned disc impeller and supplied with sterile air at a rate of 1 volume per minute. The temperature was controlled at 28° C. and the seed stage continued for 48 hours.

The seed stage (150 l) was added as inoculum to 3000 liters of the fermentation medium contained in a 5000 liter fully baffled stainless steel fermenter. The fermentation medium had the following composition:

|  | g/l |
|---|---|
| Glucose | 40.0 |
| Soybean Flour (Arkasoy 50) | 20.0 |
| $CaCO_3$ | 0.4 |
| $CoCl_2 6H_2O$ | 0.002 |
| $NaSO_4$ | 1.0 |
| Pluronic L81 antifoam prepared in tap water, pH adjust to 6.0 with 50% HCl. | 0.2% v/v |

The medium was steam sterilised in the fermenter.

After inoculation sterile air was supplied to the fermenter at a rate of 1000 liters per minute and the fermentation stirred with two vaned disc impellers 22 inches in diameter at suitable rates to maintain adequate aeration for the production culture. The temperature was maintained at 29° C. and the pH in the range 6.5–7.0, the fermentation was harvested after 68 hours.

Whole brew from a 2000 liter fermentation carried out under essentially similar conditions was combined with that from the 5000 liter fermenter and the bulk used for the extraction procedure below.

Whole brew from the fermentation (4500 liters) was clarified by filtration on a rotary pre-coat vacuum filter to yield 3800 liters culture filtrate. The culture filtrate was extracted with approximately 1/10 volume of a 0.5% solution of Aliquat 336 in dichloromethane using a continuous extraction system. (Aliquat 336 is a quaternary ammonium preparation consisting mainly of tricaprylyl methyl ammonium chloride and supplied by General Mills Chemicals Inc., Minneapolis, Minn. U.S.A.).

The dichloromethane phase was extracted into a 1/25 volume of 0.625 M sodium nitrate solution in deionised water. The phases were separated by continuous centrifugation to yield a total extract of 15.2 liters.

The aqueous phase was divided into 2 batches and further purified by treatment with aluminium hydroxide. The operation was carried out at 5° C. and the precipitate removed by centrifugation.

To the resulting combined aqueous phase (14.1 liters) was added NaCl at 50 g/l then $Na_2HPO_4$ 1.95 g/l and $NaH_2PO_4 2H_2O$ 1.77 g/l to buffer the pH of the solution at 7.0. Fine adjustment of pH was achieved by the addition of NaOH or HCl.

The solution was run onto a 15.3×80 cm Diaion HP20 column previously equilibrated in 0.05 M pH 7.0 phosphate buffer containing 5% NaCl. The column was eluted with chilled deionised water at 2 bed volumes per hour, and a single 9 liter fraction collected immediately after elution of the NaCl. Levels of NaCl in the eluates were determined by measuring the conductivity of the solution.

The 9 l of eluate from the HP20 chromatography stage were combined with 7 l of a similar solution from a previous batch and loaded into a 15.3×43 cm column of QAE Sephadex A25 (Pharmacia Ltd., Prince Regent Road, Hounslow, Middlesex, England) at 2 bed volumes per hour. The column was previously equilibrated in 0.1 M NaCl in 0.05 M sodium phosphate buffer (pH 7.5). The column was eluted with a gradient from 0.1 M to 0.7 M NaCl in 0.05 M sodium phosphate buffer. Approximately 500 ml fractions were collected and suitable fractions combined to yield a total volume of 13.1 liters.

To the 13.1 liters was added 10 g/liter NaCl and the resulting solution loaded onto a 15.3×80 cm Diaion HP20 column at 2 bed volumes per hour. This column had previously been equilibrated in 5% NaCl solution. The column was eluted with distilled water, and 8.4 liters of eluate after final elution of the NaCl were collected.

The bulk solution was filtered through a DDS type 800 membrane with a molecular weight cut off at approximately 6000. (DDS membrane from DDS RO-Division, De Danske Sukkerfabrikker, DK 4900, Nakskov, Denmark). A further 4.5 liters distilled water was added to the retentate and filtration continued until a total volume of 12.9 liters had passed the filter. The permeate (12.9 liters were concentrated by reverse osmosis until the volume of the retentate was reduced to approximately 2.5 liters.

To the 2.5 liters of concentrate was added NaCl at 50 g/liter. Further chromatography was carried out on a column (8×62 cm) packed with Diaion HP20. The concentrate was loaded at 1.16 bed volumes per hour. The column was eluted with distilled water at 1.0 bed volume per hour. After elution of the NaCl the eluate between 1060 ml and 2660 ml was collected as a bulk the pH of the resulting solution adjusted to pH 7.5 and freeze dried to yield a solid (0.8 g).

The freeze dried product (0.8 g) was dissolved in approximately 5 ml of distilled water and chromatographed on a 2.4×78 cm. Biogel P2 column (Bio Rad Laboratories, Caxton Way, Watford, Hertfordshire, England). The column was eluted with distilled water at 2 ml/minute and approximately 12 ml fractions were collected. Fractions containing MM 27696 (23–26) were combined to yield a bulk of 55 ml. The bulked fractions were concentrated by evaporation under reduced pressure and applied to a column of Dianion HP20, (2.4×36 cm) (Mitsubishi Chemicals Ltd., Agents Nippon Rensui Co., Fuji Building, 2-3 Marunouchi, 3-chrome, Chiyoda-Ku, Tokyo 100, Japan). The column was eluted with distilled water at 3 ml/minute and approximately 15 ml fractions collected. Fractions 20–24 containing MM 27696 were combined and freeze dried to yield a solid (70 mg).

27 mg of this solid were divided into three approximately equal portions and each dissolved in 0.25 ml distilled water. Each batch was then further purified by chromatography on a 12.8×500 mm Whatman semi-preparative high performance liquid chromatography column (Whatman Ltd., Springfield Mill, Maidstone, Kent, England.) containing Partisil 10 M9 ODS reversed phase material. The column was eluted with 0.01 M pH 7.0 potassium phosphate buffer. In each case the fraction containing MM 27696 was collected and the product from each chromatographic run combined to yield a total volume of 22.5 ml.

The combined fractions were concentrated by evaporation and chromatographed on a 2.4×36 cm Diaion HP20 column eluting with distilled water at 3 ml/minute. Approximately 12 ml fractions were collected, and those containing MM 27696 (13–21) were combined and freeze dried to yield a solid (10.5 mg) containing MM 27696.

$^1$H n.m.r. spectrum of disodium salt: shows characteristic signals at: δ (D$_2$O) 1.15 (3H, t, J 7.5 Hz C$\underline{H}_3$CH$_2$), 1.57 (3H, d, J 6 Hz, C$\underline{H}_3$CH), 2.38 (2H, q, J 7.5 Hz, C$\underline{H}_2$CH$_3$) and 6.10 (1H, d, J 13.5 Hz, =C$\underline{H}$.S) [ref; HOD at δ 4.67].

The antibacterial activity of the preparation of MM 27696 described in the example has been determined by the microtitre method and is reported in The Table.

EXAMPLE 2

Alkylation of the disodium salt of MM 27696 with p-nitrobenzyl bromide

A sample of the disodium salt of MM 29676 (35 mg, ca. 70% pure) was stirred with p-nitrobenzyl bromide (50 mg) in NN-dimethylformamide (3 ml) for 2 hours at room temperature. The solvent was removed in vacuo, and the residue was chromatographed on silica gel using 10%, 20% and 30% ethanol in chloroform, respectively, to elute. Fractions were monitored by t.l.c. and those containing the alkylated product were combined and concentrated in vacuo. Toluene was added to the residue and the solvent was again removed in vacuo to afford a white solid (18 mg). This product consisted of the sodium salt of p-nitrobenzyl (5R,6R)-3-[(E)-2-propionamidoethenylthio]-6-[(S)-1-hydroxysulphonyloxyethyl]-7-oxo-1-azabicyclo[3.2.0.]hept-2-ene-2-carboxylate; λ$_{max}$ (H$_2$O) 325, 266 and 220 nm; ν$_{max}$ (KBr) 1760, 1690 and 1625 cm$^{-1}$; $^1$H n.m.r.-δ (DMF-d$_7$) 1.07 (3H, t, J 7.5 Hz, C$\underline{H}_3$CH$_2$), 1.45 (3H, d, J 6 Hz, C$\underline{H}_3$CH), 2.31 (2H, q, J 7.5 Hz, C$\underline{H}_2$CH$_3$), 3.03 (1H, dd, J 19.5 and 9.5 Hz, 4-C$\underline{H}_a$), 3.73 (1H, dd J 5.5 and 11 Hz, 6-CH), 3.86 (1H, dd, J 19.5 and 8.5 Hz, 4-C$\underline{H}_b$), 4.29 (1H, m, 5-CH), 4.56 (1H, m, C$\underline{H}$CH$_3$), 5.33 and 5.57 (each 1H, d, J 13 Hz, C$\underline{H}_2$Ar), 5.95 (1H, d, J 13.5 Hz, =CH.S), 7.23 (1H, dd, J 13.5 and 11 Hz, =CH.N), 7.81 and 8.28 (each 2H, d, J 9 Hz, ArCH$_2$) and 10.53 (1H, br d, J 11 Hz, NH); $^{13}$Cn.m.r.-δ (DMF-d$_7$) 9.45 (C$\underline{H}_3$CH$_2$), 20.35 (C$\underline{H}_3$CH), 29.27 (C$\underline{H}_2$CH$_3$), 37.78 (4-C) 54.53 (6-C), 59.91. (5-C), 65.30 (C$\underline{H}_2$PNB), 69.21 (C$\underline{H}$CH$_3$), 98.01 (SC$\underline{H}$=), 121.95 (3-C), 124.14 (C-3 and C-5 on aromatic ring), 129.03 (C-2 and C-6 on aromatic ring), 133.66 (=C$\underline{H}$.N), 144.99 (C-1 on aromatic ring), 148.21 (C-4 on aromatic ring), 154.04 (2-C), 161.30 (C$\underline{O}_2$CH$_2$Ar), 171.97 (C$\underline{O}$CH$_2$CH$_3$) and 177.76 (7-C).

TABLE 1

Antibacterial Activity of MM 27696 sodium salt determined by the Microtitre Method

| Organism | MM 27696 MIC (μg/ml) |
|---|---|
| Citrobacter freundii E8 | 3.1 |
| Enterobacter cloacae N1 | 0.2 |
| Escherichia coli 0111 | 0.8 |
| Escherichia coli JT 39 | 0.2 |
| Klebsiella aerogenes A | 0.4 |
| Proteus mirabilis C977 | <0.1 |
| Proteus morganii I580 | 0.2 |
| Proteus rettgeri WM16 | 0.4 |
| Proteus vulgaris W091 | 0.4 |
| Pseudomonas aeruginosa A | 50 |
| Salmonella typhimurium CT10 | 0.2 |
| Serratia marcescens US20 | 6.2 |
| Shigella sonnei MB 11967 | <0.1 |
| Bacillus subtilis A | <0.1 |
| Staphylococcus aureus Oxford | 0.4 |
| Staphylococcus aureus Russell | 0.8 |
| Staphylococcus aureus 1517 | 100 |
| Streptococcus faecalis I | 12.5 |
| Streptococcus pneumoniae CN33 | <0.1 |
| Streptococcus pyogenes CN10 | <0.1 |
| E. coli ESS | <0.1 |

TABLE 2

β-Lactamase Inhibitory Activity of MM 27696 sodium salt (I$_{50}$ μg/ml)

| β-Lactamase | Assay | MM 27696 |
|---|---|---|
| Enterobacter | a | 0.002 |
| cloacae P99 | b | 0.25 |
| Klebsiella | a | 0.003 |
| aerogenes E70 | b | 0.4 |
| E. coli JT4 | a | 0.01 |
|  | b | 0.4 |
| S. aureus Russell | a | 0.03 |
|  | b | >50 | a = with preincubation
b = without preincubation

What we claim is:

1. A compound of the formula (VI):

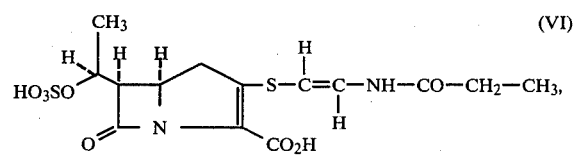

a pharmaceutically acceptable salt, the lithium salt or a pharmaceutically acceptable ester thereof, said ester being one which is convertible to the free acid or salt thereof by biological methods or chemical methods.

2. A compound according to claim 1 in the form of a pharmaceutically acceptable salt.

3. A compound according to claim 2 in the form of a di-sodium or di-potassium salt.

4. A compound according to claim 1 in the form of the p-nitrobenzyl ester.

5. A compound according to claim 1 in the form of a pharmaceutically acceptable salt selected from the group consisting of alkali metal salts and alkaline earth metal salts.

6. A compound according to claim 1 in the form of a pharmaceutically acceptable salt wherein said salt is the sodium, potassium, calcium, magnesium, ammonium, trimethylammonium, dimethylammonium, tetramethylammonium or pyrrolidine salt.

7. A compound according to claim 1 in the form of a pharmaceutically acceptable salt wherein the salt is the mono- or di-sodium or potassium salt.

8. A compound according to claim 1 in the form of an ester wherein the ester is an alkyl of up to 6 carbon atoms, an alkenyl of up to 6 carbon atoms, an alkynyl of up to 6 carbon atoms, phenyl or phenylalkyl of up to 6 carbon atoms in the alkyl moiety unsubstituted or substituted by halo, alkoxy of 1–6 carbon atoms, alkanoyl of 1–6 carbon atoms, hydroxy, alkanoyloxy of 1–6 carbon atoms, alkylamino of 1–6 carbon atoms or di-alkylamino of 1–6 carbon atoms in each alkyl moiety.

9. A compound according to claim 1 in the form of an ester wherein the ester moiety is of the formula:

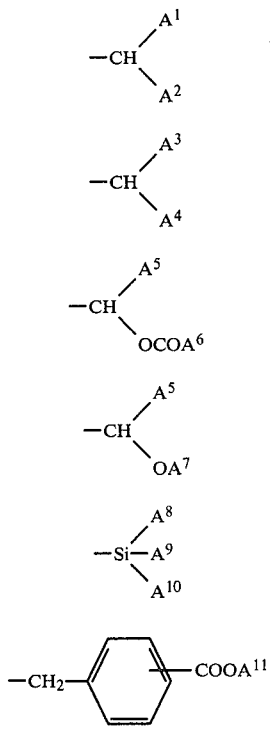

wherein $A^1$ is hydrogen, alkanoyl of 1–6 carbon atoms or alkyl of 1–6 carbon atoms unsubstituted or substituted by alkoxy of 1–7 carbon atoms, carboxylic acyloxy of 1–7 carbon atoms, alkenyl of up to 5 carbon atoms or alkynyl of up to 5 carbon atoms; $A^2$ is hydrogen or methyl; $A^3$ is phenyl unsubstituted or substituted by fluoro, chloro, bromo, nitro alkyl of 1–3 carbon atoms or alkoxy of 1–3 carbon atoms; $A^4$ is hydrogen or phenyl unsubstituted or substituted by fluoro, chloro, bromo, nitro alkyl of 1–3 carbon atoms or alkoxy of 1–3 carbon atoms; $A^5$ is hydrogen or methyl; $A^6$ is alkyl of 1–6 carbon atoms, phenyl, phenoxy, phenyl alkyl of 1–3 carbon atoms in the alkyl moiety, phenyl alkoxy of 1–3 carbon atoms in the alkoxy moiety or alkoxy of 1–6 carbon atoms or $A^5$ is joined to $A^6$ to form a phthalidyl, dimethylphthalidyl or dimethoxyphthalidyl moiety; $A^7$ is alkyl of 1–4 carbon atoms, phenyl, chlorophenyl or nitrophenyl; $A^8$ is alkyl of 1–4 carbon atoms or phenyl; $A^9$ is alkyl of 1–4 carbon atoms or phenyl; $A^{10}$ is alkyl of 1–4 carbon atoms; $A^{11}$ is alkyl of 1–4 carbon atoms; or $CHA^1A^2$ is phenacyl or bromophenacyl.

10. An ester according to claim 9 wherein $A^1$ is hydrogen, methyl, ethyl, vinyl or ethenyl; $A^2$ is hydrogen; $A^3$ is phenyl, p-bromophenyl, p-methoxyphenyl or p-nitrophenyl; $A^4$ is hydrogen; $A^5$ is hydrogen; $A^6$ is methyl, t-butyl or ethoxy or $A^6$ is joined to $A^5$ to form a phthalidyl, di-methylphthalidyl or di-methoxythalidyl moiety; and $A^7$ is methyl.

11. An ester according to claim 9 which is the methyl, ethyl or acetonyl ester.

12. An ester according to claim 9 which is the benzyl or p-nitrobenzyl ester.

13. An ester according to claim 10 wherein $A^5$ is hydrogen and $A^6$ is methyl, ethyl, n-propyl, iso-propyl, n-butyl, tert-butyl, phenyl, benzyl, methoxy, ethoxy, n-propyloxy or iso-propyloxy.

14. An ester according to claim 13 wherein $A^6$ is tert-butyl.

15. An ester according to claim 9 which is the acetoxymethyl, pivaloyloxymethyl, ethoxycarbonyloxymethyl, phthalidyl, α-ethoxycarbonyloxyethyl or α-acetoxyethyl ester.

16. An ester according to claim 9 which is the methoxymethyl ester.

17. An ester according to claim 9 which is the trimethylsilyl, tert-butyldimethylsilyl or tert-butyldiphenylsilyl ester.

18. An ester according to claim 9 which is the p-methoxycarbonylbenzyl ester.

19. An ester according to claim 9 which is the p-nitrobenzyl or phthalidyl ester.

20. A compound according to claim 1 in the form of an ester wherein the ester is an alkyl ester of 1–6 carbon atoms.

21. An ester according to claim 20 which is the methyl or ethyl ester.

22. A compound according to claim 1 or a salt or ester thereof in substantially pure form.

23. A pharmaceutical composition useful for treating bacterial infections in humans and animals and for effecting β-lactamase inhibition in humans and animals which comprises an antibacterially effective amount or a β-lactamase inhibitory amount of a compound of the formula (VI):

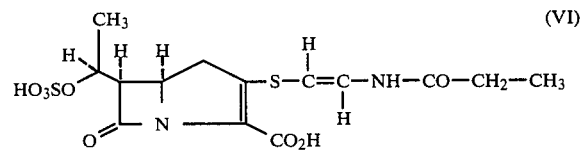

or a pharmaceutically acceptable salt or pharmaceutically acceptable ester thereof, in combination with a pharmaceutically acceptable carrier.

24. A method of treating bacterial infections in humans and animals which comprises administering to a human or animal in need thereof an antibacterially effective amount of a compound of the formula (VI):

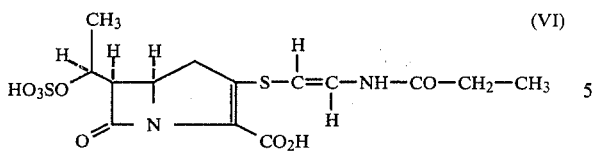

(VI)

or a pharmaceutically acceptable salt or pharmaceutically acceptable ester thereof, in combination with a pharmaceutically acceptable carrier.

25. A composition according to claim 23 wherein the compound is in the form of a pharmaceutically acceptable salt.

26. A composition according to claim 25 wherein the compound is in the form of a di-sodium or di-potassium salt.

27. A composition according to claim 23 wherein the compound is in the form of the p-nitrobenzyl ester.

28. A composition according to claim 23 wherein the compound is in the form of a pharmaceutically acceptable salt selected from the group consisting of alkali metal salts and alkaline earth metal salts.

29. A composition according to claim 23 wherein the compound is in the form of a pharmaceutically acceptable salt wherein said salt is the sodium, potassium, calcium, magnesium, ammonium, trimethylammonium, dimethylammonium, tetramethylammonium or pyrrolidine salt.

30. A composition according to claim 23 wherein the compound is in the form of a pharmaceutically acceptable salt wherein the said is the mono- or di-sodium or potassium salt.

31. A composition according to claim 23 wherein the compound is in the form of an ester, said ester being one which is convertible to the free acid or salt thereof by biological methods or chemical methods.

32. A composition according to claim 23 wherein the compound is in the form of an ester wherein the ester is an alkyl of up to 6 carbon atoms, an alkenyl of up to 6 carbon atoms, an alkynyl of up to 6 carbon atoms, phenyl or phenylalkyl of up to 6 carbon atoms in the alkyl moiety unsubstituted or substituted by halo, alkoxy of 1-6 carbon atoms, alkanoyl of 1-6 carbon atoms, hydroxy, alkanoyloxy of 1-6 carbon atoms, alkylamino of 1-6 carbon atoms or di-alkylamino of 1-6 carbon atoms in each alkyl moiety.

33. A composition according to claim 23 wherein the compound is in the form of an ester wherein the ester moiety is of the formula:

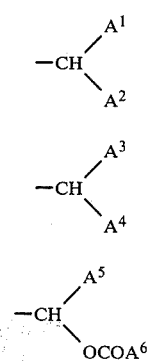

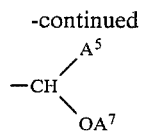

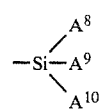

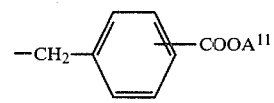

wherein $A^1$ is hydrogen, alkanoyl of 1-6 carbon atoms or alkyl of 1-6 carbon atoms unsubstituted or substituted by alkoxy of 1-7 carbon atoms, carboxylic acyloxy of 1-7 carbon atoms, alkenyl of up to 5 carbon atoms or alkynyl of up to 5 carbon atoms; $A^2$ is hydrogen or methyl; $A^3$ is phenyl unsubstituted or substituted by fluoro, chloro, bromo, nitro alkyl of 1-3 carbon atoms or alkoxy of 1-3 carbon atoms; $A^4$ is hydrogen or phenyl unsubstituted or substituted by fluoro, chloro, bromo, nitro alkyl of 1-3 carbon atoms or alkoxy of 1-3 carbon atoms; $A^5$ is hydrogen or methyl; $A^6$ is alkyl of 1-6 carbon atoms, phenyl, phenoxy, phenyl alkyl of 1-3 carbon atoms in the alkyl moiety, phenyl alkoxy of 1-3 carbon atoms in the alkoxy moiety or alkoxy of 1-6 carbon atoms or $A^5$ is joined to $A^6$ to form a phthalidyl, dimethylphthalidyl or dimethoxyphthalidyl moiety; $A^7$ is alkyl of 1-4 carbon atoms, phenyl, chlorophenyl or nitrophenyl; $A^8$ is alkyl of 1-4 carbon atoms or phenyl; $A^9$ is alkyl of 1-4 carbon atoms or phenyl; $A^{10}$ is alkyl of 1-4 carbon atoms; $A^{11}$ is alkyl of 1-4 carbon atoms; or $CHA^1A^2$ is phenacyl or bromophenacyl.

34. A composition according to claim 33 wherein $A^1$ is hydrogen, methyl, ethyl, vinyl or ethenyl; $A^2$ is hydrogen; $A^3$ is phenyl, p-bromophenyl, p-methoxyphenyl or p-nitrophenyl; $A^4$ is hydrogen; $A^5$ is hydrogen, $A^6$ is methyl, t-butyl or ethoxy or $A^6$ is joined to $A^5$ to form a phthalidyl, di-methylphthalidyl or di-dimethoxyphthalidyl moiety; and $A^7$ is methyl.

35. A composition according to claim 33 wherein the ester is the methyl, ethyl or acetonyl ester.

36. A composition according to claim 33 wherein the ester is the benzyl or p-nitrobenzyl ester.

37. A composition according to claim 34 wherein $A^5$ is hydrogen and $A^6$ is methyl, ethyl, n-propyl, iso-propyl, n-butyl, tert-butyl, phenyl, benzyl, methoxy, ethoxy, n-propyloxy or iso-propyloxy.

38. A composition according to claim 37 wherein $A^6$ is tert-butyl.

39. A composition according to claim 33 wherein the ester is the acetoxymethyl, pivaloyloxymethyl, ethoxycarbonyloxymethyl, phthalidyl, α-ethoxycarbonyloxyethyl or α-acetoxyethyl ester.

40. A composition according to claim 33 wherein the ester is the methoxymethyl ester.

41. A composition according to claim 33 wherein the ester is the trimethylsilyl, tert-butyldimethylsilyl or tert-butyldiphenylsilyl ester.

42. A composition according to claim 33 wherein the ester is the p-methoxycarbonylbenzyl ester.

43. A composition according to claim 33 wherein the ester is the p-nitrobe zyl or phthalidyl ester.

44. A composition according to claim 23 wherein the compound is in the form of an ester wherein the ester is an alkyl ester of 1-6 carbon atoms.

45. A composition according to claim 44 wherein the ester is the methyl or ethyl ester.

46. A composition according to claim 23 wherein the compound, pharmaceutically acceptable salt thereof or pharmaceutically acceptable ester thereof is in substantially pure form.

47. A composition according to claim 23 in oral administration form.

48. A composition according to claim 23 in parenteral administration form.

49. A composition according to claim 23 in topical administration form.

50. A method according to claim 24 wherein the compound is in the form of a pharmaceutically acceptable salt.

51. A method according to claim 50 wherein the compound is in the form of a di-sodium or di-potassium salt.

52. A method according to claim 24 wherein the compound is in the form of the p-nitrobenzyl ester.

53. A method according to claim 24 wherein the compound is in the form of a pharmaceutically acceptable salt selected from the group consisting of alkali metal salts and alkaline earth metal salts.

54. A method according to claim 24 wherein the compound is in the form of a pharmaceutically acceptable salt wherein said salt is the sodium, potassium, calcium, magnesium, ammonium, trimethylammonium, dimethylammonium, tetramethylammonium or pyrrolidine salt.

55. A method according to claim 24 wherein the compound is in the form of a pharmaceutically acceptable salt wherein the salt is the mono- or di-sodium or potassium salt.

56. A method according to claim 24 wherein the compound is in the form of an ester, said ester being one which is convertible to the free acid or salt thereof by biological methods or chemical methods.

57. A method according to claim 24 wherein the compound is in the form of an ester wherein the ester is an alkyl of up to 6 carbon atoms, an alkenyl of up to 6 carbon atoms, an alkynyl of up to 6 carbon atoms, phenyl or phenylalkyl of up to 6 carbon atoms in the alkyl moiety unsubstituted or substituted by halo, alkoxy of 1-6 carbon atoms, alkanoyl of 1-6 carbon atoms, hydroxy, alkanoyloxy of 1-6 carbon atoms, alkylamino of 1-6 carbon atoms or di-alkylamino of 1-6 carbon atoms in each alkyl moiety.

58. A method according to claim 24 wherein the compound is in the form of an ester wherein the ester moiety is of the formula:

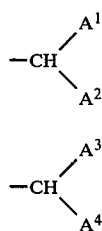

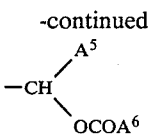

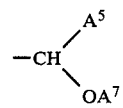

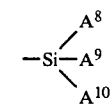

wherein $A^1$ is hydrogen, alkanoyl of 1-6 carbon atoms or alkyl of 1-6 carbon atoms unsubstituted or substituted by alkoxy of 1-7 carbon atoms, carboxylic acyloxy of 1-7 carbon atoms, alkenyl of up to 5 carbon atoms or alkynyl of up to 5 carbon atoms; $A^2$ is hydrogen or methyl; $A^3$ is phenyl unsubstituted or substituted by fluoro, chloro, bromo, nitro alkyl of 1-3 carbon atoms or alkoxy of 1-3 carbon atoms; $A^4$ is hydrogen or phenyl unsubstituted or substituted by fluoro, chloro, bromo, nitro alkyl of 1-3 carbon atoms or alkoxy of 1-3 carbon atoms; $A^5$ is hydrogen or methyl; $A^6$ is alkyl of 1-6 carbon atoms, phenyl, phenoxy, phenyl alkyl of 1-3 carbon atoms in the alkyl moiety, phenyl alkoxy of 1-3 carbon atoms in the alkoxy moiety or alkoxy of 1-6 carbon atoms or $A^5$ is joined to $A^6$ to form a phthalidyl, dimethylphthalidyl or dimethoxyphthalidyl moiety; $A^7$ is alkyl of 1-4 carbon atoms, phenyl, chlorophenyl or nitrophenyl; $A^8$ is alkyl of 1-4 carbon atoms or phenyl; $A^9$ is alkyl of 1-4 carbon atoms or phenyl; $A^{10}$ is alkyl of 1-4 carbon atoms; $A^{11}$ is alkyl of 1-4 carbon atoms; or $CHA^1A^2$ is phenacyl or bromophenacyl.

59. A method according to claim 58 wherein $A^1$ is hydrogen, methyl, ethyl, vinyl or ethenyl; $A^2$ is hydrogen; $A^3$ is phenyl, p-bromophenyl, p-methoxyphenyl or p-nitrophenyl; $A^4$ is hydrogen; $A^5$ is hydrogen; $A^6$ is methyl, t-butyl or ethoxy or $A^6$ is joined to $A^5$ to form a phthalidyl, di-methylphthalidyl or di-methoxyphthalidyl moiety; and $A^7$ is methyl.

60. A method according to claim 58 wherein the ester is the methyl, ethyl or acetonyl ester.

61. A method according to claim 58 wherein the ester is the benzyl or p-nitrobenzyl ester.

62. A method according to claim 59 wherein $A^5$ is hydrogen and $A^6$ is methyl, ethyl, n-propyl, iso-propyl, n-butyl, tert-butyl, phenyl, benzyl, methoxy, ethoxy, n-propyloxy or iso-propyloxy.

63. A method according to claim 62 wherein $A^6$ is tert-butyl.

64. A method according to claim 58 wherein the ester is the acetoxymethyl, pivaloyloxymethyl, ethoxycarbonyloxymethyl, phthalidyl, α-ethoxycarbonyloxyethyl or α-acetoxyethyl ester.

65. A method according to claim 58 wherein the ester is the methoxymethyl ester.

66. A method according to claim 58 wherein the ester is the trimethylsilyl, tert-butyldimethylsilyl or tert-butyldiphenylsilyl ester.

67. A method according to claim 58 wherein the ester is the p-methoxycarbonylbenzyl ester.

68. A method according to claim 58 wherein the ester is the p-nitrobezyl or phthalidyl ester.

69. A method according to claim 24 wherein the compound is in the form of an ester wherein the ester is an alkyl ester of 1-6 carbon atoms.

70. A method according to claim 69 wherein the ester is the methyl or ethyl ester.

71. A method according to claim 24 wherein the compound, pharmaceutically acceptable salt thereof or pharmaceutically acceptable ester thereof is in substantially pure form.

72. A method according to claim 24 wherein the administration is oral.

73. A method according to claim 24 wherein the administration is parenteral.

74. A method according to claim 24 wherein the administration is topical.

* * * * *